(12) United States Patent
Gill et al.

(10) Patent No.: US 6,490,030 B1
(45) Date of Patent: Dec. 3, 2002

(54) PORTABLE PRODUCT AUTHENTICATION DEVICE

(75) Inventors: Richard P. Gill, Ledyard, CT (US); Rakesh Vig, Durham, CT (US); J. Christopher Philips, Charlestown, RI (US); Friedrich Behringer, Old Lyme, CT (US)

(73) Assignee: Verification Technologies, Inc., Centerbrook, CT (US)

( * ) Notice: Subject to any disclaimer, the term of this patent is extended or adjusted under 35 U.S.C. 154(b) by 0 days.

(21) Appl. No.: 09/232,324

(22) Filed: Jan. 18, 1999

(51) Int. Cl.[7] .......................... G06K 9/74; G01N 21/64
(52) U.S. Cl. .......................... 356/71; 436/20; 436/24; 436/172
(58) Field of Search .......................... 356/71, 317, 394, 356/318, 417; 382/115, 116, 117, 124–127; 340/825.34; 283/68, 69, 70; 250/227.26, 227.28; 455/411; 436/20, 24, 172

(56) References Cited

U.S. PATENT DOCUMENTS

| 1,822,098 A | 9/1931 | Huntress |
| 2,265,196 A | 12/1941 | Riley |
| 2,521,124 A | 9/1950 | Miller |

(List continued on next page.)

FOREIGN PATENT DOCUMENTS

| DE | 2 118 928 | 11/1971 |
| DE | 196 17 106 A1 | 10/1997 |
| EP | 0 327 163 A2 | 9/1989 |
| EP | 0 589 991 B1 | 4/1994 |
| EP | 0 591 315 B1 | 4/1994 |
| EP | 0 736 767 A1 | 10/1996 |
| EP | 0878537 A1 | 5/1997 |
| GB | 1 334 866 | 1/1974 |
| GB | 2 258 528 A | 10/1993 |
| GB | 2 298 713 B | 9/1996 |
| GB | 2 334 574 A | 8/1999 |
| JP | 63184039 | 7/1988 |
| WO | WO 95/06249 | 2/1995 |
| WO | WO 97/31332 | 8/1997 |

OTHER PUBLICATIONS

The Invisible Barcode, downloaded from http://www.canadianpackaging.com/C . . . aging, downloaded Jul. 1999.

1st Advanced Packaging Technology Conference held Nov. 9–11, 1998, downloaded from http://auburn.main.com/tse/imi/completed/advanced–pkg–euro.html; downloaded Jul. 1999.

Phosphor Technology, downloaded from http:/www.phosphor.demon.co.uk/iruv.htm; downloaded Jul. 1999.

(List continued on next page.)

Primary Examiner—Hoa Q. Pham
(74) Attorney, Agent, or Firm—Wolf, Greenfield & Sacks, P.C.

(57) ABSTRACT

A portable product authentication device and method for analyzing key ingredients and the relative amounts of key ingredients in products which in turn enables authentication and monitoring products for authenticity, fraud and quality control is disclosed. Particular light-emissive compounds can be used to identify and quantitate the relative levels of key ingredients in the products. The invention includes a probe assembly for providing a source of light to irradiate a sample product, an optical detector to detect emitted light from the irradiated product and a controller to determine the authenticity or quality of the sample product by comparing the emitted light to a standard. A small sample of the product to be authenticated is tested on site (e.g., at the point of manufacture or at the point of distribution) thereby giving immediate feedback as to its authenticity or quality. The sample, together with the light-emissive compound may be placed on a chip. The chip, together with the small amount of sample is placed in the probe assembly.

60 Claims, 8 Drawing Sheets

U.S. PATENT DOCUMENTS

| | | | |
|---|---|---|---|
| 3,356,462 A | 12/1967 | Cooke et al. | |
| 3,412,245 A | 11/1968 | Halverson | |
| 3,444,517 A | 5/1969 | Rabinow | |
| 3,473,027 A | 10/1969 | Freeman et al. | |
| 3,500,047 A | 3/1970 | Berry | |
| 3,533,744 A | 10/1970 | Unger | |
| 3,591,283 A | 7/1971 | Peisach | |
| 3,624,644 A | 11/1971 | Higgins | |
| 3,649,464 A | 3/1972 | Freeman | |
| 3,662,181 A | 5/1972 | Hercher et al. | |
| 3,663,813 A | 5/1972 | Shaw | |
| 3,886,083 A | 5/1975 | Laxer | |
| 3,928,226 A | 12/1975 | McDonough et al. | |
| 3,992,158 A | 11/1976 | Przybylowicz et al. | |
| 3,996,006 A | 12/1976 | Pagano | |
| 4,015,131 A | 3/1977 | McDonough et al. | |
| 4,018,643 A | 4/1977 | Levine | |
| 4,038,151 A | 7/1977 | Fadler et al. | |
| 4,053,433 A | 10/1977 | Lee | |
| 4,077,845 A | 3/1978 | Johnson | |
| 4,078,656 A | 3/1978 | Crane et al. | |
| D248,044 S | 5/1978 | Odom, Jr. et al. | |
| 4,087,332 A | 5/1978 | Hansen | |
| 4,118,280 A | 10/1978 | Charles et al. | |
| 4,146,792 A | 3/1979 | Stenzel et al. | |
| 4,154,795 A | 5/1979 | Thorne | |
| 4,202,491 A | 5/1980 | Suzuki | |
| 4,235,964 A | 11/1980 | Bochner | |
| 4,243,694 A | 1/1981 | Mansukhani | |
| 4,260,392 A | 4/1981 | Lee | |
| 4,329,317 A | 5/1982 | Detweiler et al. | |
| 4,365,970 A | 12/1982 | Lawerence et al. | |
| 4,382,064 A | 5/1983 | Detweiler et al. | |
| 4,387,112 A | 6/1983 | Blach | |
| 4,439,356 A | 3/1984 | Khanna et al. | |
| 4,450,231 A | 5/1984 | Ozkan | |
| 4,451,521 A | 5/1984 | Kaule et al. | |
| 4,451,530 A | 5/1984 | Kaule et al. | |
| 4,468,410 A | 8/1984 | Zeya | |
| 4,485,308 A | 11/1984 | Rabatin | |
| 4,486,536 A | 12/1984 | Baker et al. | |
| 4,501,496 A | 2/1985 | Griffin | |
| 4,514,085 A | 4/1985 | Kave | |
| 4,540,595 A | 9/1985 | Acitelli et al. | |
| 4,557,900 A | 12/1985 | Heitzmann | |
| 4,567,370 A | 1/1986 | Falls | |
| 4,589,551 A | 5/1986 | Hellon | |
| 4,589,743 A | 5/1986 | Clegg | |
| 4,598,205 A | 7/1986 | Kaule et al. | |
| 4,620,776 A | 11/1986 | Ima | |
| 4,631,174 A | 12/1986 | Kondo | |
| 4,632,901 A | 12/1986 | Valkirs et al. | |
| 4,642,526 A | 2/1987 | Hopkins | |
| 4,657,540 A | 4/1987 | Yomiyuki et al. | |
| 4,736,425 A | 4/1988 | Jalon | |
| 4,746,631 A | 5/1988 | Clagett | |
| 4,756,557 A | 7/1988 | Kaule et al. | |
| 4,767,205 A | 8/1988 | Schwartz et al. | |
| 4,789,804 A | 12/1988 | Karube et al. | |
| 4,806,316 A | 2/1989 | Johnson et al. | |
| 4,818,677 A | 4/1989 | Hay-Kaufman et al. | |
| 4,822,746 A | 4/1989 | Walt | |
| 4,865,812 A | 9/1989 | Kuntz et al. | |
| 4,882,195 A | 11/1989 | Butland | |
| 4,889,365 A | 12/1989 | Chouinard | |
| 4,897,173 A | 1/1990 | Nankai et al. | |
| 4,916,056 A | 4/1990 | Brown et al. | |
| 4,921,280 A | 5/1990 | Jalon | |
| 4,927,180 A | 5/1990 | Trundle et al. | |
| 4,948,442 A | 8/1990 | Manns | |
| 4,966,856 A | 10/1990 | Ito et al. | |
| 4,983,817 A | 1/1991 | Dolash et al. | |
| 5,005,873 A | 4/1991 | West | |
| 5,018,866 A | 5/1991 | Osten | |
| 5,030,421 A | 7/1991 | Muller | |
| 5,030,832 A | 7/1991 | Williams et al. | |
| 5,039,490 A | 8/1991 | Marsoner et al. | |
| 5,047,215 A | 9/1991 | Manns | |
| 5,049,673 A | 9/1991 | Tsien et al. | |
| 5,093,147 A | 3/1992 | Andrus et al. | |
| 5,106,582 A | 4/1992 | Baker | |
| 5,114,864 A | 5/1992 | Walt | |
| 5,118,349 A | 6/1992 | Jalon | |
| 5,128,243 A | 7/1992 | Potter et al. | |
| 5,128,882 A | 7/1992 | Cooper et al. | |
| 5,135,569 A | 8/1992 | Mathias | |
| 5,139,812 A | 8/1992 | Lebacq | |
| 5,143,853 A | 9/1992 | Walt | |
| 5,147,042 A | 9/1992 | Levy | |
| 5,152,287 A | 10/1992 | Kane | |
| 5,176,257 A | 1/1993 | Levy | |
| 5,194,289 A | 3/1993 | Butland | |
| 5,200,051 A | 4/1993 | Cozzette et al. | |
| 5,208,630 A | 5/1993 | Goodbrand et al. | |
| 5,244,636 A | 9/1993 | Walt et al. | |
| 5,244,813 A | 9/1993 | Walt et al. | |
| 5,246,869 A | 9/1993 | Potter et al. | |
| 5,250,264 A | 10/1993 | Walt et al. | |
| 5,252,494 A | 10/1993 | Walt | |
| 5,260,032 A | 11/1993 | Muller | |
| 5,264,103 A | 11/1993 | Yoshioka et al. | |
| 5,272,090 A | 12/1993 | Gavish et al. | |
| 5,279,967 A | 1/1994 | Bode | |
| 5,282,894 A | 2/1994 | Albert et al. | |
| 5,286,286 A | 2/1994 | Winnik et al. | |
| 5,292,000 A | 3/1994 | Levy | |
| 5,292,855 A | 3/1994 | Krutak et al. | |
| 5,298,741 A | 3/1994 | Walt et al. | |
| 5,313,264 A | 5/1994 | Ivarsson et al. | |
| 5,319,436 A | 6/1994 | Manns et al. | |
| 5,320,814 A | 6/1994 | Walt et al. | |
| 5,321,261 A | 6/1994 | Valenta | |
| 5,336,714 A | 8/1994 | Krutak et al. | |
| 5,338,066 A | 8/1994 | Gundjian | |
| 5,338,067 A | 8/1994 | Gundjian | |
| 5,360,628 A | 11/1994 | Butland | |
| 5,366,902 A | 11/1994 | Cox et al. | |
| 5,409,583 A | 4/1995 | Yoshioka et al. | |
| 5,409,666 A | 4/1995 | Nagel et al. | |
| 5,418,136 A | 5/1995 | Miller et al. | |
| 5,418,855 A | 5/1995 | Liang et al. | |
| 5,421,869 A | 6/1995 | Gundjian et al. | |
| 5,424,959 A | 6/1995 | Reyes et al. | |
| 5,429,952 A | 7/1995 | Garner et al. | |
| 5,438,403 A | 8/1995 | Hoshino et al. | |
| 5,450,190 A | 9/1995 | Schwartz et al. | |
| 5,457,527 A | 10/1995 | Manns et al. | |
| 5,468,650 A | 11/1995 | Skov et al. | |
| 5,494,638 A | 2/1996 | Gullick | |
| 5,496,701 A | 3/1996 | Pollard-Knight | |
| 5,498,549 A | 3/1996 | Nagel et al. | |
| 5,512,490 A | 4/1996 | Walt et al. | |
| 5,516,362 A | 5/1996 | Gundjian et al. | |
| 5,521,984 A | 5/1996 | Denenberg et al. | |
| 5,525,516 A | 6/1996 | Krutak et al. | |
| 5,545,567 A | 8/1996 | Gretillat et al. | |
| 5,546,471 A | * 8/1996 | Merjanian ................ 356/71 |
| 5,547,501 A | 8/1996 | Maruyama et al. | |
| 5,568,177 A | 10/1996 | Talvalkar et al. | |
| 5,569,317 A | 10/1996 | Sarada et al. | |
| 5,574,790 A | 11/1996 | Liang et al. | |

| | | |
|---|---|---|
| 5,582,697 A | 12/1996 | Ikeda et al. |
| 5,589,350 A | 12/1996 | Bochner |
| 5,599,578 A | 2/1997 | Butland |
| 5,608,225 A | 3/1997 | Kamimura et al. |
| 5,611,433 A | 3/1997 | Levy |
| 5,614,008 A | 3/1997 | Escano et al. |
| 5,618,682 A | 4/1997 | Scheirer |
| 5,625,706 A | 4/1997 | Lee et al. |
| 5,631,170 A | 5/1997 | Attridge |
| 5,632,959 A | 5/1997 | Mohajer |
| 5,641,640 A | 6/1997 | Hanning |
| 5,650,062 A | 7/1997 | Ikeda et al. |
| 5,651,869 A | 7/1997 | Yoshioka et al. |
| 5,665,151 A | 9/1997 | Escano et al. |
| 5,666,417 A | 9/1997 | Liang et al. |
| 5,671,288 A | 9/1997 | Wilhelm et al. |
| 5,673,338 A | 9/1997 | Denenberg et al. |
| 5,710,626 A | 1/1998 | O'Rourke et al. |
| 5,711,915 A | 1/1998 | Siegmund et al. |
| 5,716,825 A | 2/1998 | Hancock et al. |
| 5,719,948 A | 2/1998 | Liang |
| 5,728,350 A | 3/1998 | Kinoshita et al. |
| 5,736,342 A | 4/1998 | Van Wie et al. |
| 5,753,511 A | 5/1998 | Selinfreund |
| 5,762,873 A | 6/1998 | Fanning et al. |
| 5,773,808 A | 6/1998 | Laser |
| 5,774,160 A | 6/1998 | Gundjian |
| 5,776,713 A | 7/1998 | Garner et al. |
| 5,784,193 A | 7/1998 | Ferguson |
| 5,786,182 A | 7/1998 | Catanzariti et al. |
| 5,786,509 A | 7/1998 | Belding et al. |
| 5,800,785 A | 9/1998 | Bochner et al. |
| 5,807,625 A | 9/1998 | Amon et al. |
| 5,811,152 A | 9/1998 | Cleary |
| 5,818,582 A | 10/1998 | Fernandez et al. |
| 5,822,473 A | 10/1998 | Magel et al. |
| 5,837,042 A | 11/1998 | Lent et al. |
| 5,851,489 A | 12/1998 | Wolf et al. |
| 5,856,174 A | 1/1999 | Lipshutz et al. |
| 5,861,618 A | 1/1999 | Berson |
| 5,867,586 A | 2/1999 | Liang |
| 5,874,219 A | 2/1999 | Rava et al. |
| 5,879,946 A * | 3/1999 | Weeks et al. ................. 436/60 |
| 5,879,951 A | 3/1999 | Sy et al. |
| 5,919,712 A | 7/1999 | Herron et al. |
| 5,922,188 A | 7/1999 | Ikeda et al. |
| 5,922,550 A | 7/1999 | Everhart et al. |
| 5,922,591 A | 7/1999 | Anderson et al. |
| 5,922,594 A | 7/1999 | Löfås |
| 5,923,413 A | 7/1999 | Laskowski |
| 5,927,547 A | 7/1999 | Papen et al. |
| 5,939,024 A | 8/1999 | Robertson et al. |
| D414,272 S | 9/1999 | O'Bear et al. |
| 5,955,352 A | 9/1999 | Inoue et al |
| 5,955,729 A | 9/1999 | Nelson et al. |
| 5,961,926 A | 10/1999 | Kolb et al. |
| 5,966,205 A * | 10/1999 | Jung et al. .................... 356/71 |
| 5,989,835 A | 11/1999 | Dunlay et al. |
| 5,998,128 A | 12/1999 | Roelant |
| 6,001,573 A | 12/1999 | Roelant |
| 6,232,124 B1 * | 5/2001 | Selinfreund ................. 436/20 |

OTHER PUBLICATIONS

Fluorescent Inks downloaded from http://www.uvp.com/html/inks.html; downloaded Jul. 1999.
V.L. Engineering, Our Products; downloaded from http://www.vlengineering.com/products/wizard_PV6A downloaded Jul. 1999.
Junior LB 9509, the portable luminometer:, downloaded from http://www.berthold.com.au/bioanalytical_pages/LB9509.html, downloaded Oct. 26, 1999.
R. Service, Microchip Arrays Put DNA on the Spot, Oct. 16, 1998, vol. 282 Science, pp. 396–399.
R. Service, Coming Soon: The Pocket DNA Sequencer, Oct. 16, 1998, vol. 282, Science, pp. 399–402.
I. Amato, Fomenting a Revolution, in Miniature, Oct. 16, 1998, vol. 282, Science, pp. 402–404.
Web Site Disclosure: Packard Instrument Company: Tools for Life Science Research, pp. 1–2.
Biocode product literature, "Covert Product Identification".
Freemantle, M., "Downsizing Chemistry: Chemical analysis and synthesis on micriships promise a variety Of potential benefits", C&EN London, pp. 27–36, Feb. 22, 1999.
Furneaux, R.C., et al., "The formation of controlled–porosity membranes from anodically oxidized aluminum,", Nature, vol. 337, No. 6203, pp. 147–149, Jan. 12, 1989.
Glabe, C.G., et al., "Preparation and Properties of Fluorescent Polysaccharides", Analytical Biochemistry, vol. 130, pp. 287–294, 1983.
Minta, A., et al., "Fluorescent Indicators for Cytosolic Calcium Based on Rhodamine and Fluorescein Chromophores", Journal of Biol. Chem., vol. 264, No. 14, pp. 8171–8178, May 15, 1989.
Schauer, C.L., et al., "Cross–reactive optical sensor arrays", ACS Meetings, San Francisco National Meeting, Downloaded from http://schedule.acs.org/cgi–bin/ACS/perso . . . , Mar. 7, 2000.
Skolnick, A., "Russian and US Researchers Develop 'Biochips' for Faster, Inexpensive Biomedical Tests", JAMA, vol. 275, No. 8, pp. 581–582, Feb. 28, 1996.
Stanley, D., "UT scientists engineer a tiny arbiter of taste", Austin American Statesman Newspaper, p. B1, Jul. 26, 1998.
Stringer, "Photonics Center launches three new companies", Mass. High Tech., p. 11, Apr. 26–May 2, 1999.
Biacore Website, "Sensor chips for Biacore analysis systems", downloaded from webmaster.bia@eu.biacore.com; undated.
Biacore Website, "Principles of BIAtechnology", downloaded from webmaster.bia@eu.biacore.com, Undated.
Biacore Website, "protein binding", downloaded from webmaster.bia@eu.biacore.com, undated.
Biodiscovery website, "Inventing Expression Bioinformatics", undated.
Cambridge Healthtech Institute Website, downloaded from www.healthtec.com, undated.
Corning Microarray Technology Website, "CMT–GAPS Coated Slides—FAQ's", downloaded from www.cmt.corning.com/dev/company info/who/techno . . . , Oct. 26, 1999.
Genometrix Website, undated.
Packard Website, "The Biochip Arrayer", downloaded from www.packardinst.com/prod_serv/–Biochiparrayer.htm, Oct. 26, 1999.
Bruno, A., et al., "All–Solid–State Miniaturized Fluorescence Sensor Array for the Determination of Critical Gases and Electrolytes in Blood," Analytical Chemistry, 69: 507–513, Feb. 1, 1997.
AOAC Official Methods of Analysis, 1990, pp. 752–754.
Barrett, "Molecular Fingerprinting of Food Bourne Pathogens," CDD IFT Symposium, Jun. 21–22, 1996.
Bock, G., et al., "Photometric Analysis fo Antifading Reagents for Immunofluorescence with Laser and Conventional Illumination Sources," Journal of Histochemistry and Cytochemistry, 33: 699–705 (1985).

Chan, et al., Biochem, Biophys, Acta, vol. 204, p. 252, 1970.
Constant, et al., ACS Abstract, Issue of Chemical and Engineering News, Aug. 25, 1994.
Coons, et al., J. Exp. Med., vol. 91, pp. 1–14, 1950.
Crossley et al., Journal of the Chemical Society, Perkin Transactions 2, 1615 (1994).
Dragoco Report, pp. 12–13, 1990.
Furomoto et al., IEEE, J. Quantum Electron, QE–6, 262 (1970).
Gill, D., "Inhibition of fading in fluorescence microscopy of fixed cells," Dept. of Physics, Ben Gurion University, Israel (Jul. 1978).
Huff, J., "Enhancement of Specific Immunofluorescent Findings with Use of a Para–Phenylenediamine Mounting Buffer," Journal of Investigative Dermatology, 78: 449–450 (1982).
Iatridou, H., et al., Cell Calcium, vol. 15, pp. 190–198, 1994.
Johnson, G.D., et al., "Fading of Immunofluorescence during Microscopy: a Study of the Phenomenon and its Remedy," Journal of Immunological Methods, 55: 231–242 (1982).
Johnson, G.D., et al., "A Simple Method of Reducing the Fading of Immunofluorescence During Microscopy," Journal of Immunological Methods, 43: 349–350 (1981).
Larsen, R., et al., "Spectroscopic and Molecular Modeling Studies of Caffeine Complexes with DNA Intercalators," Biophysical Journal, 70:443–452 (Jan. 1996).
Lee, S.P., et al., "A Fluorometric Assay for DNA Cleavage Reactions Characterized with BamHl Restriction Endonuclease," Analytical Biochemistry, 220: 377–383 (1994).
Platt, J. L., et al., "Retardation of Fading and Enhancement of Intensity of Immunofluorescence by p–Phenylenediamine," Journal of Histochemistry and Cytochemistry, 31:840–842 (1983).
Practical Fluorescence, Second Edition, G.G. Guilbault, Editor, Marcel Dekker, Inc., p. 32, 1990.
Raybourne, "Flow Cytometry in Food Microbiolog," IFT Symposium FDA, Jun. 21–22, 1996.
Stryer, L., "Fluorescence Energy Transfer as a Spectroscopic Ruler," Ann. Rev. Biochem., 47:819–46.
Uchiyama, H., et al., "Detection of Undegraded Oligonucleotides in Vivo Fluorescence Resonance Energy Transfer," Journal of Biological Chemistry, 271: 380–384, Jan. 1996).
Wittwer, C.T., et al., "Continuous Fluorescence Monitoring of Rapid Cycle DNA Amplification," BioTechniques, 22:130–138 (Jan. 1997).

* cited by examiner

PORTABLE PRODUCT AUTHENTICATION DEVICE

BACKGROUND OF THE INVENTION

This invention is in the general field of devices and methods for authenticating sample compositions.

Authenticating and monitoring products to discriminate between very similar complex mixtures is useful for various reasons. For example, the use of counterfeit substances (e.g., misbranded material from a competitor or misformulated material from a licensee/franchisee) should be detected to preserve the integrity of a brand. Also, low quality substances (e.g., diluted or misformulated product) should be quickly and conveniently detected for appropriate correction.

Commonly assigned U.S. Pat. No. 5,753,511, which is herein incorporated by reference in its entirety, discloses an automated method of developing a database to store information for "fingerprint"-type analysis of products (even as to product lot numbers and batch). The automated analysis is a method of evaluating and discriminating products, even within a narrow field or industry, competing and otherwise, e.g., to establish authenticity or point of origin of the product. The invention therein relates to an automated method for identifying key ingredients and/or the relative amounts of key ingredients in products using light-emissive compounds.

The laboratory equipment used to authenticate the sample referred to in '511 is not easily and cost effectively transported. Thus, determining product authenticity on site, either at manufacturing points or at distribution points, is impractical. With regard to distribution of counterfeit substances or production of misformulated material from a licenser/franchiser, the brand owner may not desirably spontaneously check product authenticity on site.

Furthermore, a processing plant, for example, may have numerous continuous processes being performed at any given time. It may be desirable to test the product for purity or quality, for example, as the product is being produced. With relatively large, expensive laboratory equipment, this is not possible. As a result, the process must cease, sample product must be sent to a remote site for testing and the process may not resume until the samples have been tested.

SUMMARY OF THE INVENTION

According to one aspect of the invention, a portable product authentication device is provided. The device includes a base unit having a flexible conduit and a probe assembly coupled to the flexible conduit. The probe assembly has a light source for irradiating a sample to be authenticated with a predetermined wavelength of light. The device further includes an optical detector for detecting at least one emitted wavelength of light generated by the sample in response to the irradiating wavelength of light to provide a sample characteristic. A controller is disposed within the base unit and communicates with the probe assembly for receiving the sample characteristic and comparing the sample characteristic to a fingerprint. In one embodiment, the controller is located at a site remote from the probe assembly and may comprise a database of stored fingerprints. In one embodiment, the light source is a light-emitting diode. In another embodiment, the light source is a fiber optic cable operatively connected to a light-emitting diode. In yet another embodiment, a fiber optic cable is disposed within the probe assembly and is operatively connected to the optical detector for receiving emitted light generated by the sample and transmitting to the optical detector. Alternatively, the optical detector is disposed within the probe assembly.

In an important embodiment, the device includes a receptacle for interchangeably receiving one of a plurality of light sources. Each of the light sources is selected to emit a desired wavelength of light based on a desired sample to be authenticated.

In another embodiment, the device may also include an emission filter for filtering undesired wavelengths of light from the at least one emitted wavelength of light generated by the sample in response to the irradiating wavelength of light and/or a source filter for filtering undesired wavelengths of light generated from the light source. In yet another embodiment, the probe assembly is adapted to interchangeably receive one of a plurality of emission filters, and/or one of a plurality of source filters. Each emission filter is selected to filter undesired wavelengths of light based on a desired sample to be authenticated and each source filter is selected to filter undesired wavelengths of light based on a selected light source.

In another embodiment, the optical detector detects a quantity of the at least one emitted wavelength of light generated by the sample. Alternatively, the optical detector detects a change in quantity over time of the at least one emitted wavelength of light generated by the sample. The optical detector detects a characteristic of an authentic sample to provide the fingerprint and may perform a plurality of detections on a single sample to be authenticated. The fingerprint may include a range of acceptable fingerprints.

In yet another embodiment, the probe assembly further includes a holder adapted to receive the sample. The probe assembly may include a reflector to reflect light emitted from the light source toward the sample.

In another aspect of the invention, a probe assembly for detecting a characteristic of a sample to be authenticated is provided. The probe assembly includes a hand-held probe body and a light source disposed in the body for irradiating the sample with a predetermined wavelength of light. An optical detector is disposed in the body for detecting at least one emitted wavelength of light generated by the sample in response to the irradiating wavelength of light to provide a sample characteristic.

In one embodiment, the light source is a light-emitting diode. In another embodiment, the probe assembly includes a light-emitting diode receptacle formed in the body for interchangeably receiving one of a plurality of light-emitting diodes. Each of the light-emitting diodes is selected to emit a desired wavelength of light based on a desired sample to be authenticated.

In another embodiment, an emission filter disposed in the body for filtering undesired wavelengths of light from the at least one emitted wavelength of light generated by the sample in response to the irradiating wavelength of light. A source filter may be disposed in the body for filtering undesired wavelengths of light generated from the light source. In an important embodiment, the probe assembly includes an emission filter receptacle formed in the body for interchangeably receiving one of a plurality of emission filters and/or a source filter receptacle formed in the body for interchangeably receiving one of a plurality of source filters. Each emission filter is selected to filter undesired wavelengths of light based on a desired sample to be authenticated and each source filter is selected to filter undesired wavelengths of light based on a selected light source.

In yet another embodiment, the probe assembly further includes a holder adapted to receive the sample. The probe assembly may include a reflector to reflect light emitted from the light source toward the sample.

In yet another aspect of the invention, a kit for detecting a characteristic of a sample to be authenticated is provided. The kit includes a hand-held probe body having a plurality of receptacles and at least one light-emitting diode for irradiating the sample with a predetermined wavelength of light. Each light-emitting diode is adapted for insertion into one of the receptacles and is selected based on a desired wavelength of light to be emitted. Each desired wavelength is based on a desired sample to be authenticated. An optical detector for detecting at least one emitted wavelength of light generated by the sample in response to the irradiating wavelength of light is also provided. The probe body may also include a reflector for reflecting light emitted from the light source toward the sample. In one embodiment, the kit further includes at least one emission filter for filtering undesired wavelengths of light from the at least one emitted wavelength of light generated by the sample in response to the irradiating wavelength of light and/or at least one source filter for filtering undesired wavelengths of light generated from the light-emitting diode. Each filter is adapted for insertion into one of the receptacles. The kit may further include at least one light-emissive compound. Each light-emissive compound is adapted for reaction with a selected sample to be authenticated.

The kit may further include a holder adapted for insertion into the probe body. The holder is adapted for holding the light-emissive compound and the sample. The kit may also be provided with a carrying case.

In yet another aspect of the invention, a method for detecting a characteristic of a sample to be authenticated using a portable authentication device is disclosed. The device has a probe assembly having a light source for irradiating a sample to be authenticated with a predetermined wavelength of light and an optical detector for detecting at least one emitted wavelength of light generated by the sample in response to the irradiating wavelength of light to provide a sample characteristic. The method includes the steps of detecting background light with the optical detector, adding a light-emissive compound to an authentic product sample to form an authentic sample mixture, irradiating the authentic sample mixture with an irradiating wavelength of light, detecting one of a quantity and a change in quantity over time of light generated by the authentic sample mixture in response to the irradiating wavelength of light to provide a fingerprint, adding a light-emissive compound to a test product sample to form a test sample mixture, irradiating the test sample mixture with an irradiating wavelength of light, detecting one of a quantity and a change in quantity over time of light generated by the test sample mixture in response to the irradiating wavelength of light to provide a test sample characteristic, comparing the test sample characteristic to the fingerprint to determine whether the test sample is authentic.

In an important embodiment, the irradiating step and the detecting step for both the authentic sample mixture and the test sample mixture occurs in close spatial and temporal proximity. In another embodiment, when the test sample is not authentic, the method further includes the step of communicating with a remote computer and reading a stored fingerprint to determine the identity of the test sample.

In another embodiment both a quantity and a change in quantity over time of light generated by the authentic sample mixture may be detected.

In another embodiment, the method further includes the step of communicating with a controller having a database of a plurality of fingerprints. The communication occurs after a determination that the test sample is not authentic based on the comparison and wherein the step of communicating includes the step of comparing the test sample characteristic to the database of fingerprints.

In yet another embodiment, a plurality of detections on one of the authentic sample and test sample is performed.

According to another aspect of the invention, a chip is provided. The chip is a substrate and plurality of different light-emissive compounds attached to a surface of a substrate. The compounds are attached in a manner whereby they can interact with interaction partners, such interaction altering light emission from the light-emissive compounds, versus light emission from the light-emissive compounds absent interaction. Each of the different light-emissive compounds is attached at a location discrete from attachment of all other of the difference light-emissive compounds. The substrate is free of interference with light emission from the light-emissive compound in the presence of the interaction and in the absence of the interaction. In one embodiment, the plurality of compounds is selected from the group consisting of three different light-emissive compounds, four different light-emissive compounds, five different light-emissive compounds, six different light-emissive compounds, seven different light-emissive compounds, eight different light-emissive compounds, and nine different light-emissive compounds. In one important embodiment, the light-emissive compounds are dyes. The chip can define a plurality of microwells. The discrete location of attachment of each of the different light-emissive compounds can be confined to a microwell or several microwells. In a preferred embodiment, the chip has one or more markings for locating the position of each of the light-emissive compounds on the chip and/or for identifying what different light-emissive compounds are on the chip. The light-emissive compounds can be covalently or non-covalently attached to the chip.

In an important embodiment, the different light-emissive compounds in the chip are preselected and are at a preselected concentration to interact with a known standard and create a preselected pattern of light emission when the surface is contacted with the known standard characteristic of the known standard. In this instance, the marking in the chip can identify the chip as specific for the known standard.

According to another aspect of the invention, a method is provided for determining relatedness of a sample to a standard. The method involves providing a sample mixture comprising the sample applied to the surface of any of the chips described above. The sample mixture then is irradiated with a plurality of irradiating wavelengths of light. At least one emitted wavelength of light, but more typically a plurality of such wavelengths, is monitored to establish a sample emission profile. A standard fingerprint characteristic of a standard mixture is provided, the standard mixture comprising the standard applied to the surface of chip, and the standard fingerprint being generated by irradiating the standard mixture with the irradiating wavelengths and monitoring the at least one emitted wavelength in response thereto. The sample emission profile is then compared with the standard fingerprint to determine the relatedness of the sample on the standard. The sample can be applied to the surface of the chip as a microdot. In an important embodiment, the chip comprises microwells containing the light-emissive compounds, and the sample is applied to the surface of the chip as a microdot. In this embodiment, the microdrop can be permitted to spread across the surface of the chip to occupy the microwells, preferably in a manner whereby the sample is contained non-overlapping in discrete microwells once it has spread. A microchip with a wetable surface is particularly desirable in this embodiment.

According to an other aspect of the invention, a kit is provided. The kit is a package which contains a plurality of discrete substrates, each of the substrates containing or having attached thereto an identical set of 3–9 light-emissive compounds. The set is selected to interact with a known standard and create a preselected pattern of light emission when irradiated with at least one wavelength of light in the presence of one interaction. The package also contains instructions indicating that the substrates are for use with a known standard or samples for which the relatedness of the samples to the known standard is to be determined. The substrates can be constructed and arranged for use with the portable product authentication device of the invention.

In another aspect of the invention, a probe assembly for detecting a characteristic of a sample to be authenticated is provided. The probe assembly includes a hand-held probe body, a light source disposed in the body for irradiating the sample with a predetermined wavelength of light, and a plurality of fiber optic cables disposed in the body and communicating with at least one optical detector. The fiber optic cables are adapted and arranged to receive light emitted from a corresponding sample placed on a chip.

Various embodiments of the present invention provide certain advantages and overcome certain drawbacks of the conventional techniques. Not all embodiments of the invention share the same advantages and those that do may not share them under all circumstances. This being said, the present invention provides numerous advantages including the noted advantage of on-site testing.

Further features and advantages of the present invention as well as the structure and operation of various embodiments of the present invention are described in detail below with reference to the accompanying drawings.

DETAILED DESCRIPTION

The invention features a portable product authentication device and method for analyzing key ingredients and the relative amounts of key ingredients in products which in turn enables authentication and monitoring products for authenticity, fraud and quality control. Particular light-emissive compounds can be used to identify and quantitate the relative levels of key ingredients in the products. The invention includes a probe assembly for providing a source of light to irradiate a sample product, an optical detector to detect emitted light from the irradiated product and a controller to determine the authenticity or quality of the sample product by comparing the emitted light to a standard. A small sample of the product to be authenticated is tested on site (e.g., at the point of manufacture or at the point of distribution) thereby giving immediate feedback as to its authenticity or quality. It is to be appreciated that the term "authentic", or any derivative thereof, means an identification as being genuine or without adulteration and may also mean, in certain contexts, as falling within a range of acceptable quality.

Light-emissive compounds are involved in light emission in response to irradiation with light of a different wavelength. Light emission of interest can be a result of phosphorescence, chemiluminescence, or, more preferably, fluorescence. Specifically, the term "light-emissive compounds," as used herein, means compounds that have one or more of the following properties: 1) they are a fluorescent, phosphorescent, or luminescent; 2) react, or interact, with components of the sample or the standard or both to yield at least one fluorescent, phosphorescent, or luminescent compound; or 3) react, or interact, with at least one fluorescent, phosphorescent, or luminescent compound in the sample, the standard, or both to alter emission at the emission wavelength. "Fingerprint," refers to the light emission intensity and/or intensity decay from one or more light-emissive compounds in combination with a standard (e.g., authentic) product. Accordingly, each product can have a particular fingerprint. A "fingerprint emission profile" is an assembly of fingerprints of a liquid sample of a product in combination with a series (or profile) of different light-emissive compounds.

The term "sample characteristic" refers to the light emission intensity and/or intensity decay from one or more light-emissive compounds in combination with a sample product.

The term "key ingredient," as used herein, means a component included in a composition of a product that is important in identifying the particular product.

The term "trace compound," as used herein, means a compound that is present in low concentrations (e.g., at ppm or ppb levels) in a product that is related, for example, to a particular key ingredient. The trace compound can be introduced at the source of the key ingredient or during the manufacture of the product.

Figure 1:
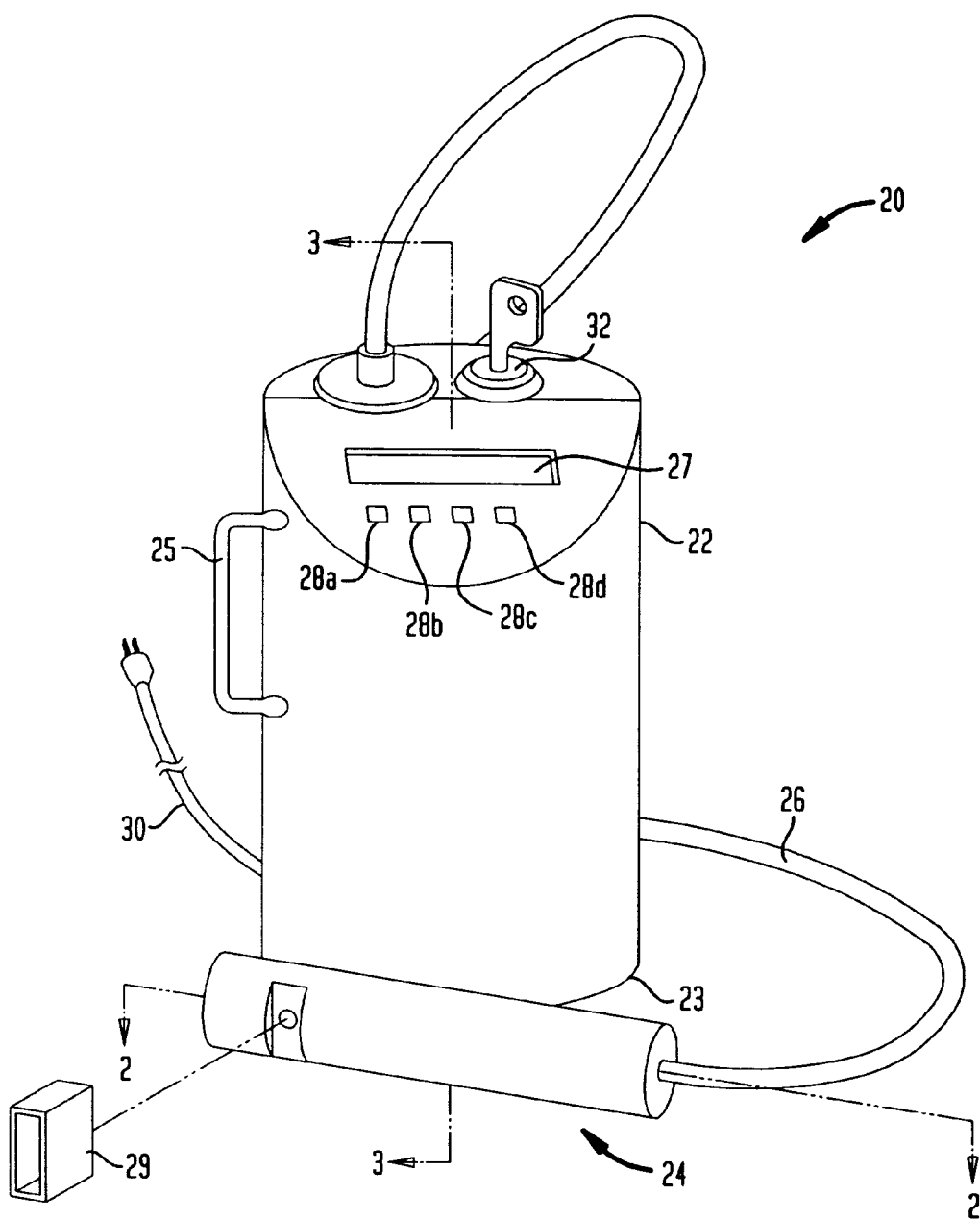
FIG. 1 is a diagrammatic representation of one embodiment of a portable product authentication device according to the present invention.

In one embodiment, as illustrated in FIG. 1, the portable product authentication device is a table-top device operatively connected to a hand-held probe. The device 20 includes a base unit 22, having a base surface 23, and may include a handle 25 for easy transportation. The base unit 22 is coupled to a hand-held probe assembly 24 via a flexible conduit 26. The flexible conduit allows easy manipulation and articulation of the probe assembly 24 into any desired orientation. The base unit 22 includes a display 27 and at least one, and preferably four, control switches 28a–28d. Power to the device 20 may be provided through a suitable power cord 30, or, alternatively, may be powered with batteries, such as rechargeable batteries. A lockout device may also be provided to selectively permit or deny use of the device. In the example described herein, the lockout device includes a key-lock switch 32. Alternatively, a password may be used. In this example, the password may be a switching of switches 28a–28d in a predetermined sequence. A sample holder 29, or cuvette, for receiving the sample to be tested is insertable into the probe assembly.

Figure 2:
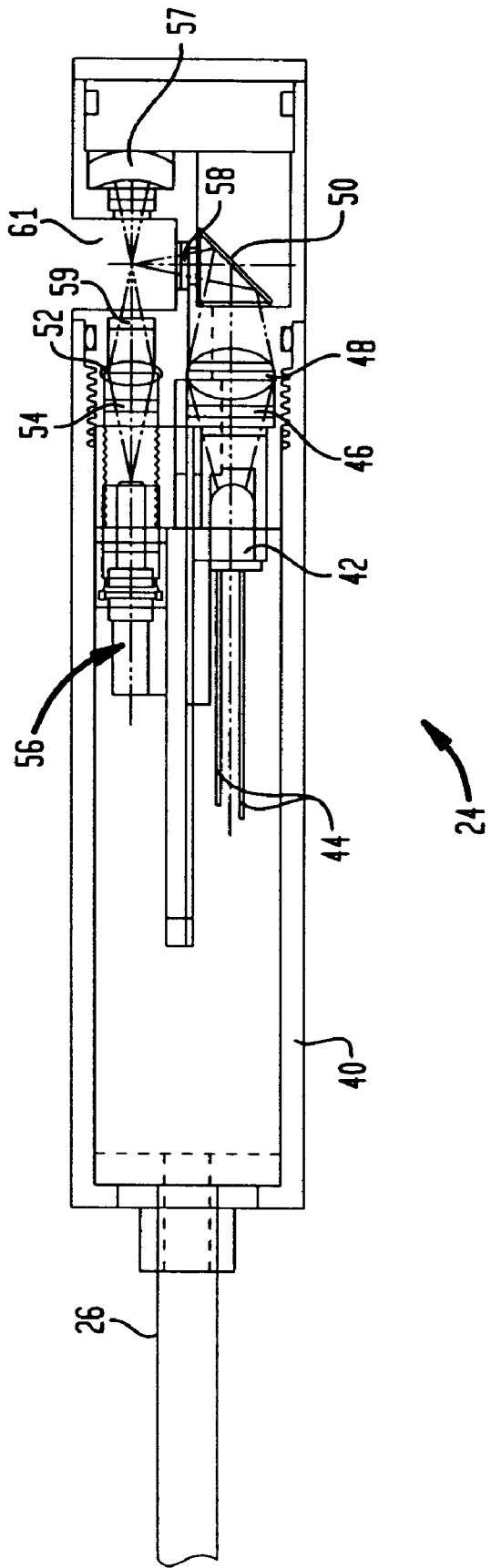
FIG. 2 is a cross-sectional view of a probe assembly taken along line 2—2 of FIG. 1.

The hand-held probe assembly 24, as best shown in the cross-sectional view of FIG. 2, directly interacts with the sample to be authenticated. In this embodiment, the probe assembly 24 includes a probe body 40, which may be a unitary body or may be formed with a plurality of discrete body parts. The probe body includes a light source disposed therein. In a preferred embodiment, the light source includes a light-emitting diode 42, which may or may not be an infrared light-emitting diode. In either case, the selected light-emitting diode is matched to the excitation wavelength of the light-emissive compound. The leads 44 of the light-emitting diode are connected, through the conduit, to the base unit 22 to receive power for excitation. The probe assembly further includes a source filter 46, such as bandpass or cutoff filter, to isolate wavelengths of light from the light-emitting diode. A lens 48, such as a symmetric convex lens having a 10 mm focal length with a 10 mm diameter, focuses light emitted from the light-emitting diode onto a right-angle prism 50. In one particular embodiment, the right-angle prism is an 8 mm×8 mm×8 mm prism.

The probe assembly 24 further includes a second lens 52, which may be similar to the first lens 48, for focusing light onto an optical detector (not shown in FIG. 2). An emission filter 54, such as a bandpass or cutoff filter, is used to isolate excitation wavelengths from emission spectra due to light emission from the sample. The filter 54 is positioned adjacent the lens 52, but may be in any location, provided certain undesired excitation wavelengths are isolated from the optical detector. A fiber optic cable 56 is disposed within the probe assembly 24 and fits within conduit 26 to operatively connect with the optical detector within base unit 22. The probe assembly 24 further includes a concave mirror reflector 57 to target the light toward the sample. In this particular embodiment, the reflector is an aluminum-coated concave mirror having a 9 mm diameter. The probe assembly may be adapted and sized for direct insertion into a sample to be tested. A port 58 is formed in the probe assembly to allow light from the light-emitting diode to irradiate the sample and another port 59 formed in the probe assembly to allow detection of emitted light from the sample. In a preferred embodiment, the probe assembly 24 may include an opening 61 adapted to receive the holder 29 (not shown in FIG. 2).

Figure 3:
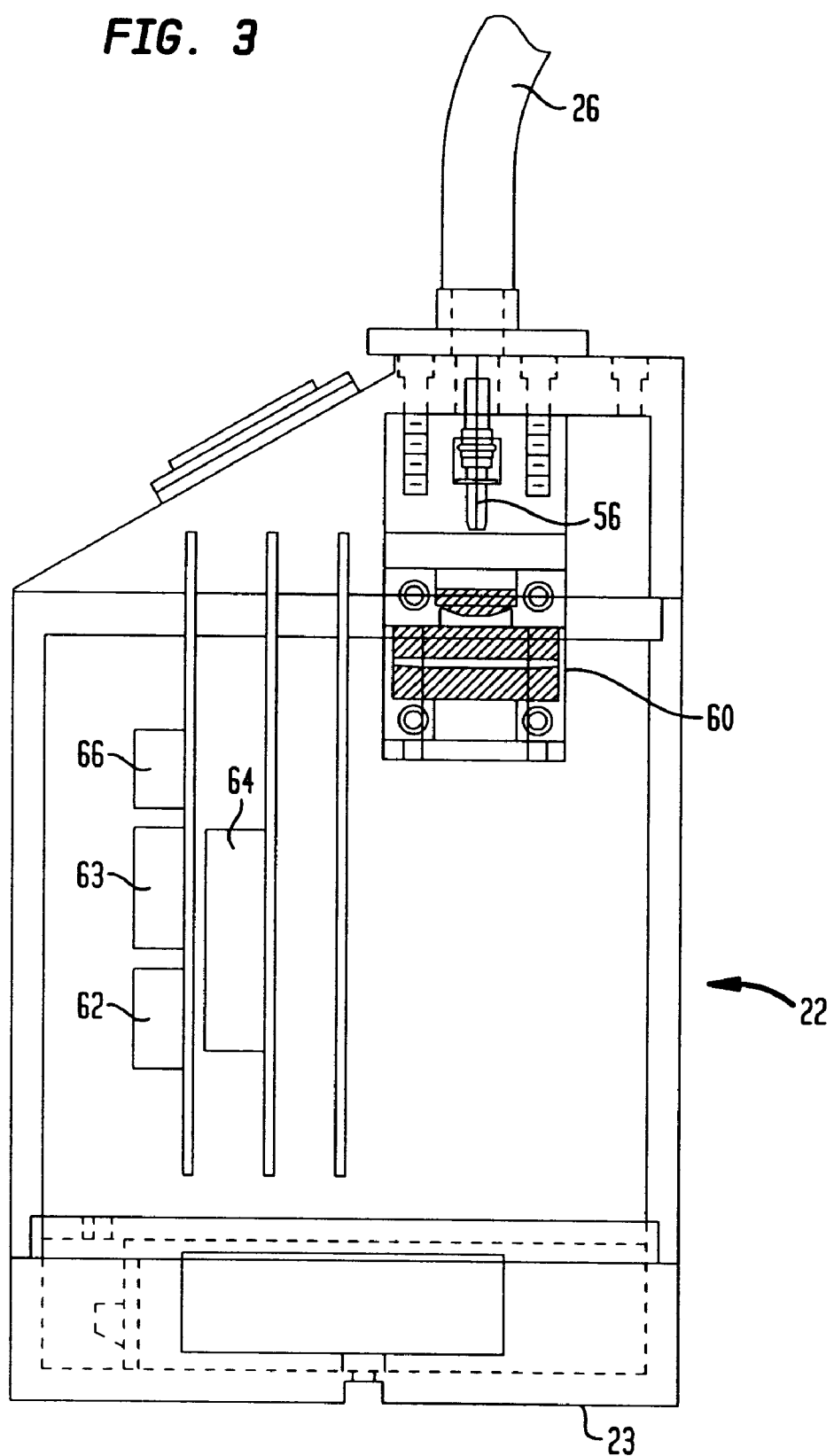
FIG. 3 is a cross-sectional view of a base unit taken along line 3—3 of FIG. 1.

Turning now to FIG. 3, which is a cross-sectional representation of the base unit 22 taken along line 3—3 of FIG. 1, the base unit 22 includes an optical detector 60 operatively coupled to the fiber optic cable 56. The optical detector 60 in turn is coupled to a suitable electronic circuit board 62, which receives electrical signals from the optical detector 60.

In one embodiment, the circuit board may include a controller 63, such as a TDS 2020 data logger, manufactured by Triangle Digital Services, LTD, London, England, and modem 64 to communicate with a database located at a remote location. Alternatively, the circuit board may include a memory device such as a read-only memory chip 66 or may communicate with a CD-ROM, for example, which stores fingerprint data.

Although the probe assembly shown and described herein is operatively connected to the base unit 22, all components necessary to test a sample for authenticity may be contained within the base unit directly. In such an embodiment, the base unit 22 includes a light source, suitable lens and filters, and an optical detector. An opening is also formed in the base unit to receive the sample to be tested.

In operation, the key lock switch is turned on to power up the device 20. Switch 28a is actuated, which causes the light-emitting diode 42 to excite and emit light which is then ultimately received by optical detector 60. The device 20 then calculates the amount of background light surrounding the probe assembly 24.

A sample mixture is made using the techniques described in U.S. Pat. No. 5,753,511 in which a light-emissive compound is mixed with a sample to form the sample mixture. In general, a sample of the product and the light-emissive compound are mixed. The light-emissive compounds and key ingredients in the product are allowed to react for a period of time and temperature that is specific for each product and light-emissive compound, for example, until light emission from the mixture no longer changes with time.

The sample is then irradiated with an irradiating wavelength of light emitting from the light-emitting diode. Specifically, the light is filtered using the source filter to obtain desired wavelengths of light and is passed and focused by the lens. The light is then reflected and refracted through the prism and is focused onto the sample mixture. The irradiated sample then emits a predetermined wavelength of light, based on the wavelengths of light being emitted from the light-emitting diode as well as the compounds used and key ingredients in the mixture. Change in light emission due to the presence of key ingredients in the product can be determined, from the formula $[(Fd-Fp)/Fd] \times 100$, where the light emission of the light-emissive compound in the absence of product is Fp, and the light emission after exposing the light-emissive compound to the product is Fd. The light emission changes as a result of interactions of the light-emissive compound with key ingredients in the product. The emission filter then filters undesired wavelengths of light emitting from the sample. The light is then directed to the fiber optic cable, which transmits the light to the optical detector in the base unit. The optical detector then generates a voltage level indicative of the wavelengths of light emitted from the sample, and converts the signal into a sample characteristic. The sample characteristic is then compared with a fingerprint of a standard to determine the authenticity of the sample. This may be accomplished by directly storing standard fingerprint data within the memory of the base unit.

In another illustrative example of the operation of the device, on-site determination of a fingerprint of an authentic sample mixture performed. The same or similar light-emissive compound is added to a authentic sample to form an authentic sample mixture. This authentic sample mixture is irradiated in the same way that the test sample mixture is irradiated. The light generated by the authentic sample mixture in response to the irradiating wavelength of light is then detected by the optical detector to provide a fingerprint.

According to the present invention, the device 20 is self-calibrating for surrounding light, temperature and other conditions. In addition, the device may compensate for degradation of the light-emitting diode, the electronics or the optical detector, for example. It has been found that a light-emissive compound may emit light at two-different wavelengths. While the value of the wavelength may change due to the above noted factors, it has been found that the ratio between two wavelengths remains relatively constant.

Thus, during on-site measurements, this ratio may be used, rather than the actual value, to determine whether the suspect sample is authentic. Thus, any variability due to a comparison of on-site data to stored data is removed. If the actual values of the emitted wavelengths were used, then an erroneous determination may result because the on-site sample characteristic may not be the same as the fingerprint, yet the sample may indeed be authentic. As previously stated, if the sample turns out to be non-authentic, then using the ratio, a determination as to the sample identity may be made by scanning the database communicating with the host computer.

It is to be appreciated that the quantity of light generated by the sample mixtures is detected. However, according to the present invention, a change in the quantity of light emitted over time may be used to provide the sample characteristic. Alternatively, both the quantity and change in quantity may be used to provide the sample characteristic.

In another embodiment of the operation of the device, the detection of both the authentic sample mixture and the test sample mixture occurs in close spatial and temporal proximity. This provides a basis for eliminating many variations that may occur if the samples were tested at different times or at different locations. This can only be accomplished with the use of a portable authentication device.

It is also to be appreciated that the sampling rate may be changed such that a plurality of sample readings are taken on a specific sample. In a preferred embodiment, about 10,000 readings are taken. Thus, a high degree of confidence is obtained in providing the sample characteristics. Further, it is to be appreciated that the fingerprint may include a range of acceptable fingerprints for a given product. Thus, quality assurance may be provided.

Figure 4:
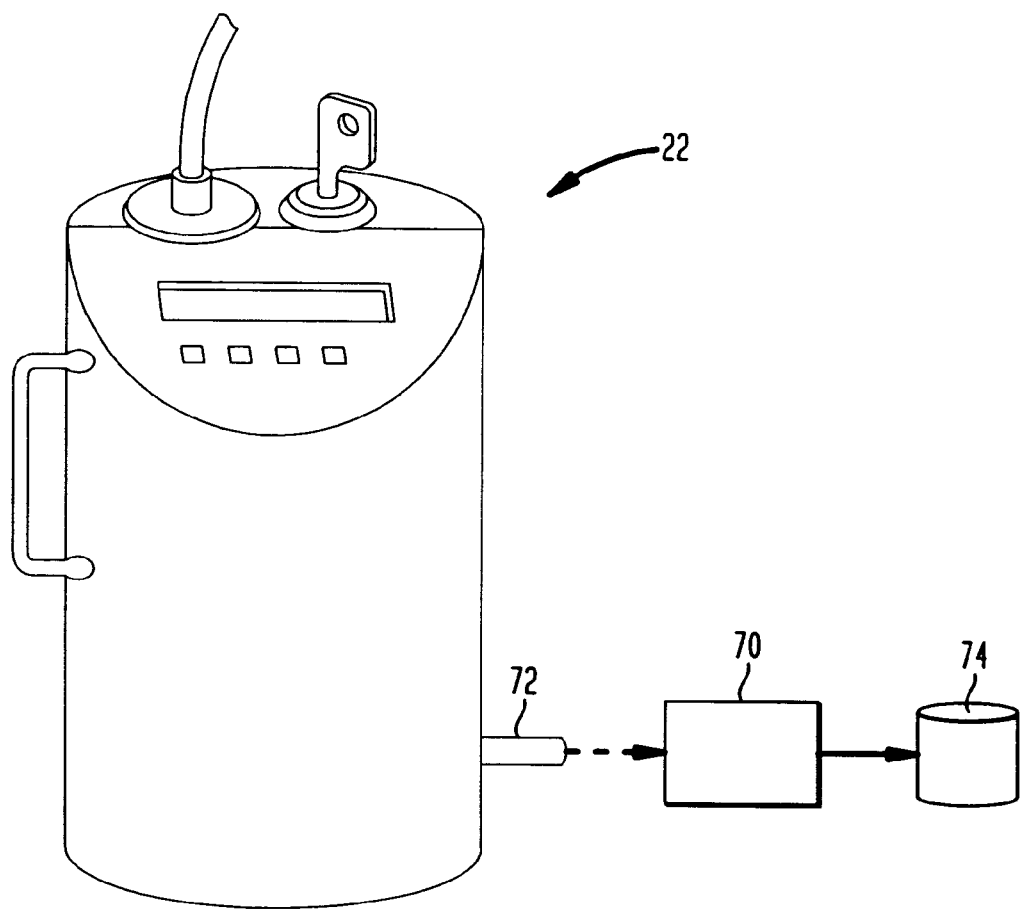
FIG. 4 is a diagrammatic representation of another embodiment of the portable product authentication device.

Turning now to FIG. 4, which is an alternative embodiment of the present invention, the base unit 22 communicates with a host computer 70 via a data cable 72 through, for example, the modem 64. Of course, those skilled in the art will recognize in view of this disclosure that other communication links may be used, such as a direct data link, satellite transmission, coaxial cable transmission, fiber optic transmission or cellular or digital communication. The communication link may be a direct line or through the Internet. The host computer 70 also communicates with a database 74 which stores a plurality of fingerprints. In this embodiment, when the test sample is determined to be not authentic, the base unit 22 communicates with the host computer 70 to determine the identity of the sample that has been tested. That is, assuming that the sample to be authenticated turns out not to be authentic as compared to the fingerprint, then the base unit communicates with the host computer to identify the sample characteristic based on a plurality of stored fingerprints. The fingerprint stored in the database may or may not be similar to the fingerprint of the authentic sample tested on site.

Figure 5:
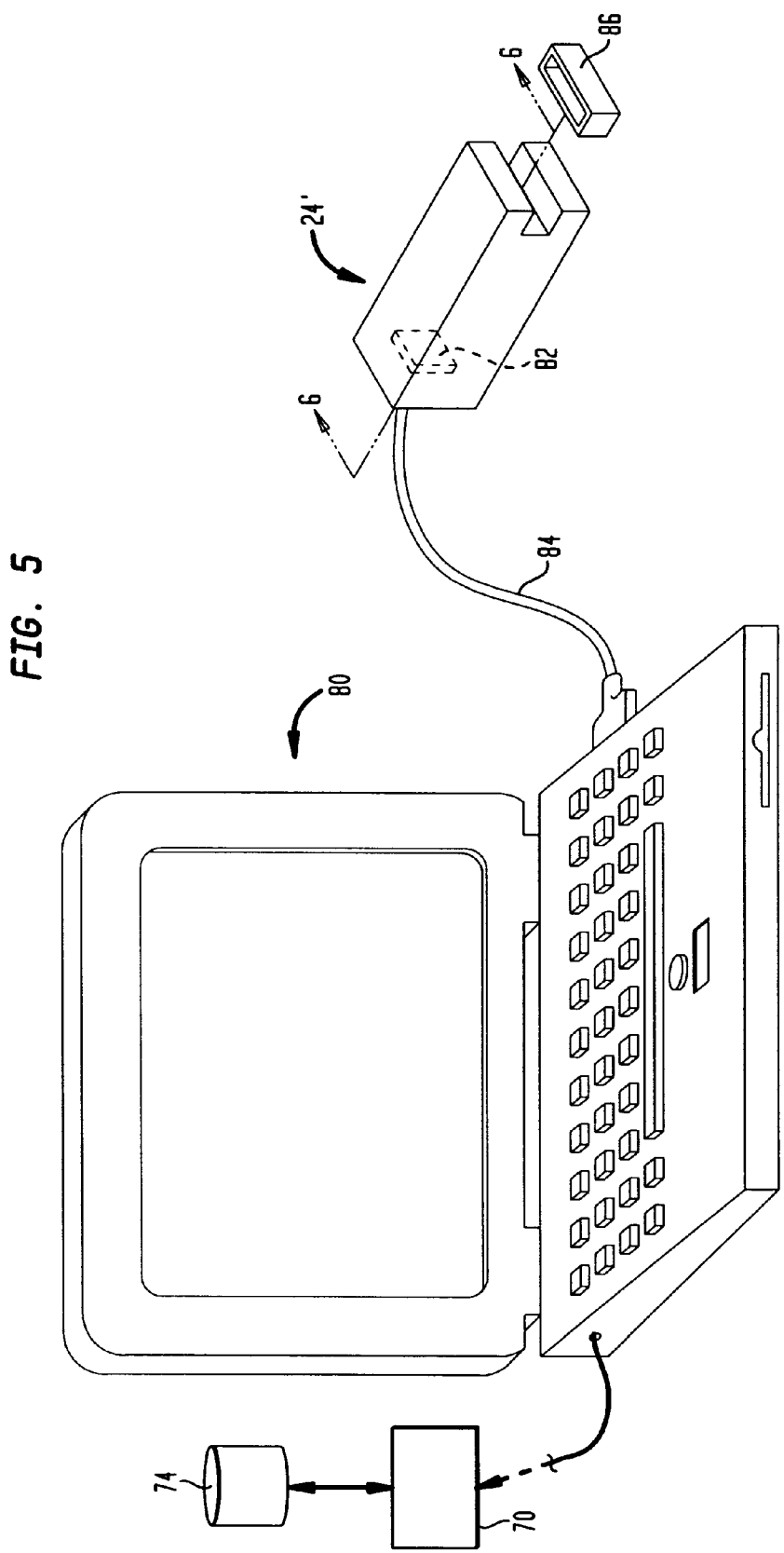
FIG. 5 is a diagrammatic representation of yet another embodiment of the portable product authentication device.

Turning now to FIG. 5, an alternative embodiment of the present invention is shown. In this example, the base unit is a laptop computer 80 or similar device, such as a desktop computer or workstation. A probe assembly 24' is coupled directly to the laptop computer 80. In this example, the computer 80 receives electrical signals from the probe assembly 24' as well as transmits electrical signals to the probe assembly 24' and may or may not communicate with the host computer 70 as desired. Each of the functions discussed above with reference to FIG. 1 may be programmed into the computer 80 so that the keyboard, mouse, or other input device may be used to control the probe assembly.

Figure 6:
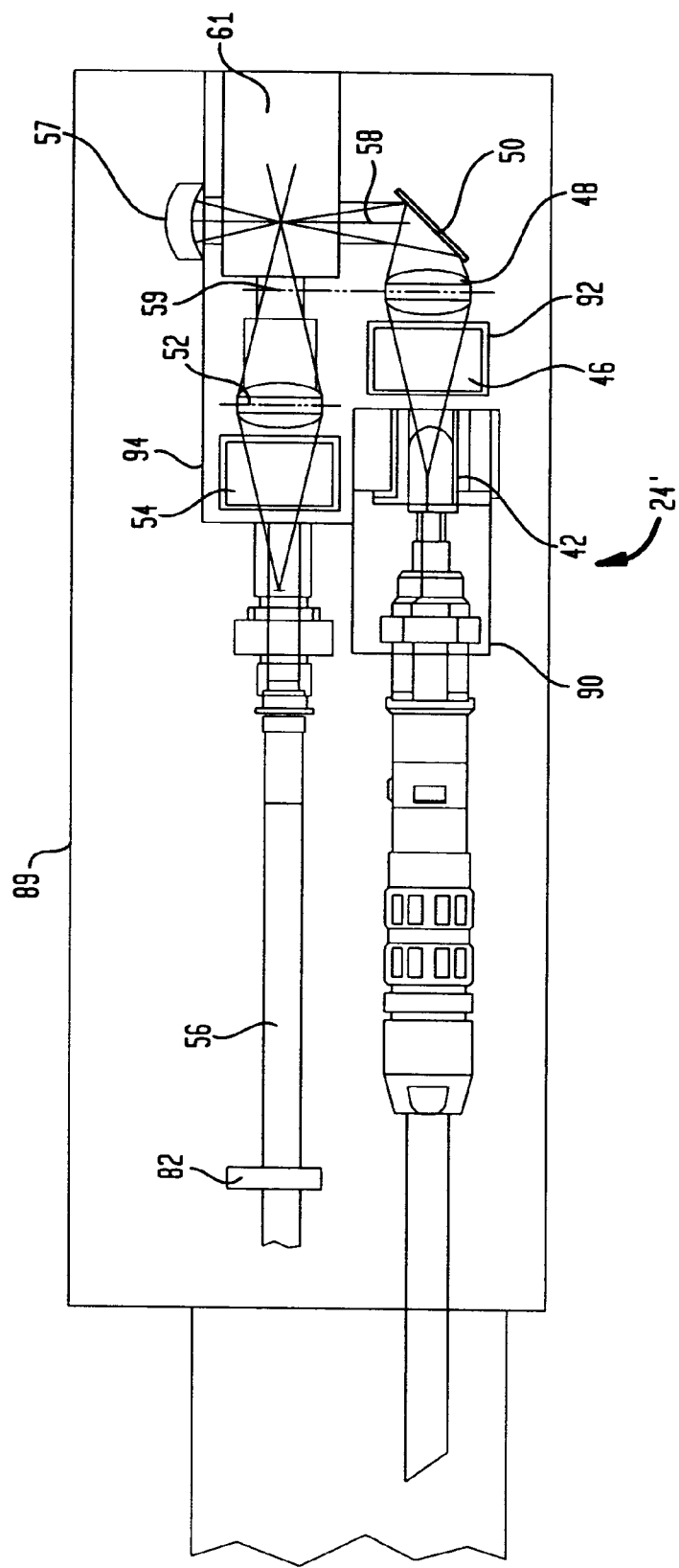
FIG. 6 is a cross-sectional view of a probe assembly taken along line 6—6 of FIG. 5.

As best shown in FIG. 6, which is a cross-sectional view of the probe assembly 24', the probe assembly 24' includes an optical detector 82 disposed therein for converting the light emitted from the sample to an electrical signal. The electrical signal is then transported through a suitable cable 84 to the laptop computer 80. Thus, rather than have a separate base unit, the testing is controlled with the laptop computer 80. In addition, as previously described, the laptop computer may include its own database to determine whether or not the sample being tested is authentic, or alternatively, may communicate via a modem to the host computer 70 to scan the database 74 for fingerprints.

Continuing with reference to FIG. 6, the probe assembly includes the previously described elements, particularly the light-emitting diode, the source filter, the first lens, the prism, the reflector, the second lens and the emission filter. In this particular example, the fiber optic cable 56 is contained within the probe assembly and transmits the light from the emission filter to the optical detector 82. However, the optical detector 82 may be positioned immediately adjacent the emissions filter 54 as desired. Further, in this example, as shown in FIGS. 5 and 6, the probe assembly is adapted to receive a cuvette 86 (see FIG. 5) in which the sample mixture is placed. The cuvette is typically a quartz material having a hollowed-out container section.

The probe assembly 24' includes a body 89 that may include receptacle 90 adapted to interchangeably receive one of a plurality of light-emitting diodes. Similarly, the probe assembly may include other receptacles 92, 94 adapted to interchangeably receive one of a plurality of source filters as well as one of a plurality of emission filters, respectively. It should be appreciated that the light-emitting diode must emit a wavelength of light corresponding to the light-emissive compound added to the sample. Thus, the type of light-emitting diode required depends upon the light-emissive compound selected for use with the sample. Similarly, the filters (the source filter and emissions filter) must correspond to the particular light-emitting diode selected.

Figure 8:
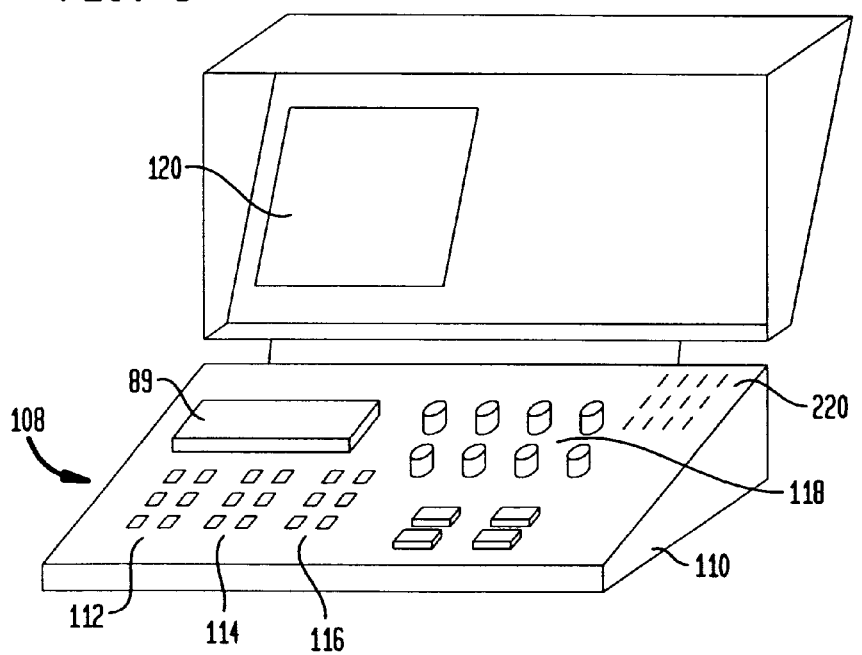
FIG. 8 is a diagrammatic representation of a kit for detecting product authenticity according to the present invention.

Thus, in one particular embodiment of the present invention, as shown in FIG. 8 a kit 108 for detecting the authenticity and/or quality of a sample is provided. The kit may be packaged in a suitable carrying case 110 having a probe body 89 such that a plurality of light-emitting diodes 112 together with corresponding source filters 114 and emissions filters 116, respectively, are provided. Further, a selection of light-emissive compounds 118 may be also provided. A chart, database, spreadsheet, instructions or other source of information 120 may be provided indicating corresponding light-emitting diodes, filters and light-emissive compounds as a function of the sample to be tested.

Although the light-emitting diode, source filter, and emissions filter are interchangeable into the probe assembly, it is to be appreciated that an entire probe assembly having discrete components (light-emitting diode, source filter, emissions filter) may be provided. Thus, a plurality of different probe assemblies having different combinations of light-emitting diodes, source filters, and emissions filters may be provided.

The probe assembly discussed with reference to FIG. 6 may also be used to detect the presence of an authentic sample or the quality of the sample directly without utilizing a holder, such as the cuvette. In this case, the tip of the probe assembly is placed directly into the sample mixture. Further, in a continuous process, a stream of material may flow through the opening in the probe assembly such that authentication or quality assurance may be determined while a production process is occurring. In this example, however, the light-emissive compound must be added upstream of the probe assembly and should be done in a relatively small batch process such that the sample undergoing test is not distributed.

It is to be appreciated further still that the sample to be tested may be either a liquid or a dry powder material, for example.

Figure 7:
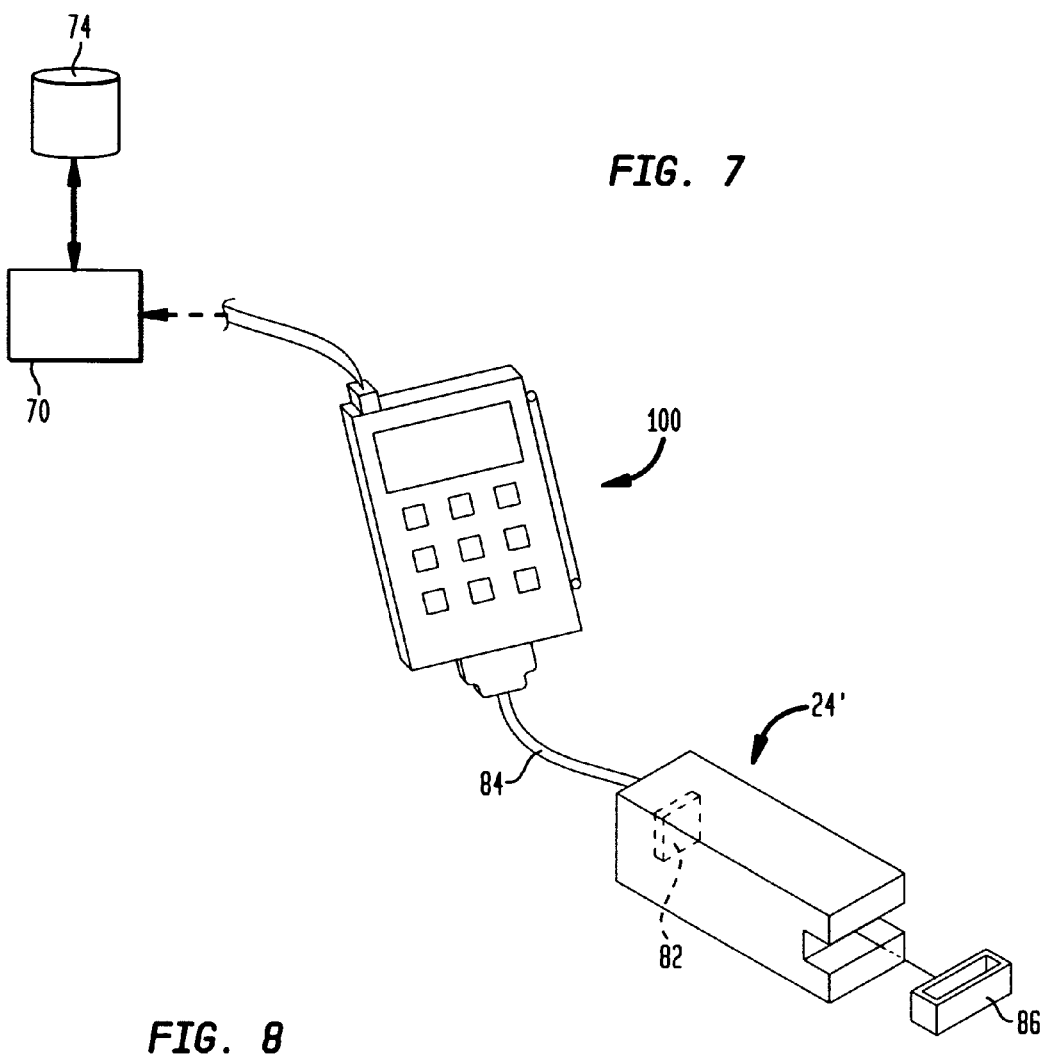
FIG. 7 is a diagrammatic representation of yet another embodiment of the portable product authentication device.

In yet another embodiment as shown in FIG. 7, the base unit is a hand-held microprocessor device 100, such as a PALM PILOT® or other data logger, which receives the signal from the optical detector indicating the sample characteristic. The probe assembly 24' communicates directly with the PALM PILOT®, which, in turn, may communicate with the host computer 70 and database 74 via any suitable means such as a modem or Internet access, for example. As discussed above with reference to FIG. 5, each of the input or control functions may be programmed into the PALM PILOT® so that the keyboard, "pen", or other input device may be used to control the probe assembly.

Rather than provide a sample mixture in a holder for detection by the probe assembly, the light-emissive compound (or dye) may be formed on a chip and the sample to be authenticated could be placed on the chip. The chip, together with the small amount of sample is placed in the probe assembly. The chip useful according to the invention may be employed in the device of the invention or also may be used in stationary, non-portable devices. The chip has the advantage of being small, requiring very little light-emissive compound, and requiring very little of the sample to be measured (e.g., a microdrop). The chip also can be used to store preselected dyes in a preselected array at preselected concentrations. The chips also make transporting of such dyes for use according to the invention very easy.

Figure 9:
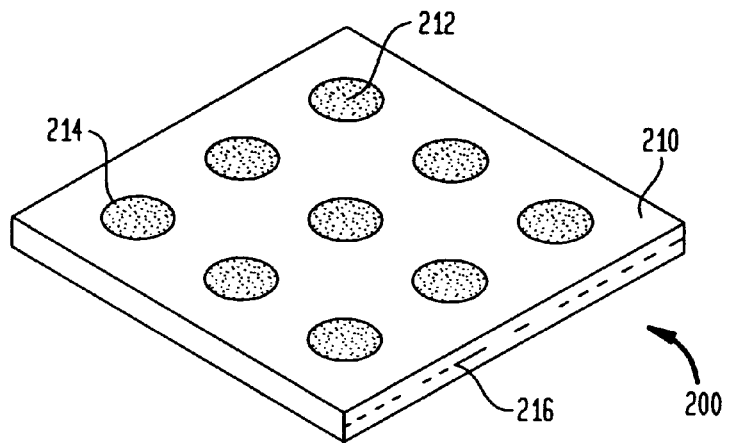
FIG. 9 is a diagrammatic representation of a chip having light-emissive compound thereon according to the present invention; and, FIG. 10 is a diagrammatic representation of yet another embodiment of the probe assembly according to the present invention.

In the embodiment described with reference to FIG. 9, each chip 200 is a substantially flat article of very small dimensions, preferably less than a centimeter, less than 5 millimeters, and even small than a millimeter. The chip is formed of a substrate 210 which can be virtually any material, provided that the material does not interfere with the light-emission altering interaction between the light-emissive compound and the standard or the sample to be measured. Examples of useful materials are polycarbonates, silicone diodes, metals, delron plastics, polystyrene and polyethylene. The light-emissive compounds 212 may be attached to the chips through any physical/chemical means, including covalent and noncovalent bonds. For example, the dyes can be dissolved in a solvent, and then applied at a preselected concentration to the surface of the chip. The solvent then is evaporated away, leaving the dyes noncovalently attached to the surface of the chip. The solvent can have the ability to etch the surface of the chip, thereby enhancing the attachment of the dye to the surface of the chip. In another embodiment, the dyes can be covalently attached to the surface of the chip. Some light-emissive compounds have groups reactive under appropriate conditions with groups on the surface of the chip, which may be reactive groups of the chip per se, or may be linker molecules attached to the surface of the chip. Homobifunctional and heterobifunctional linkers for tethering to the surface of a material are well-known to those of ordinary skill of the art. As described in the example below, an ester bond may be used, for example, to attach the dye to the chip. It is particularly preferred to employ a reactive group of the dye remote from the portion of the dye which interacts with the standard, whereby the dye, once covalently attached to the chip, is free to interact appropriately with the standard or sample.

In a particularly preferred embodiment, the chip has microwells 214. Certain prefabricated materials which are commercially available are provided with such microwells. In this manner, a particular dye can be confined to a particular microwell. The chip also can be provided with stipples or markings 216 specific for the chip, whereby the chip can be identified as carrying particular dyes and whereby the dyes may be located on the chip at a particular location with reference to the markings. Thus, in a preferred embodiment, a chip has between three and nine dyes, each different dye located and concentrated within a single microwell on the surface of the chip, covalently attached thereto. The dyes preferably are of the highest fluorescence, such as fluorescein or Bodipy. The dyes are of preselected concentrations to permit authentication of a preselected material.

The kit 108, shown in FIG. 8, may also contain a plurality of discrete substrates 220, each of the substrates containing or having attached thereto an identical set of 3–9 light-emissive compounds. The set is selected to interact with a known standard and create a preselected pattern of light emission when irradiated with at least one wavelength of light in the presence of one interaction. The instructions 120 indicate that the substrates are for use with a known standard or samples for which the relatedness of the samples to the known standard is to be determined.

To prepare the microchip, borosilicate glass wafers are first cleaned with an acid, rinsed with double distilled water (three times), silanized with 3-aminopropyl-1-trethoxysilane (Sigma, St Louis, Mo.), then heated at 25–80° C. for 3–5 hours. The organosilane provides the amine functional group for cross reactivity for attaching the light-emissive compounds. The amines should be at a density of 10 pmol of amines/cm2 on the chip.

To place the light-emissive compound on the microchip, 6-carboxyfluorescein, succinimidyl ester 10 mg from (Molecular Probes, Eugene, Oreg.) was used with the following procedure. The borosilicate chip is pre treated with a buffer (0.1M sodium bicarbonate, pH 8.3–9.0). The 6-carboxyfluoresecein is made to a dilution of 10 mg/ml in DMSO (dimethylsulfoxide). 100 uls was placed on the borosilicate glass wafer and set to react for 1–3 hours at 4° C. This reaction should take place in a water-saturated environment. The reaction may be stopped by the addition of 100 uls of 1.5M hydroxylamine, pH 8.5. The chip is then washed, preferably three times, with 500 uls of distilled water to remove unreacted light-emissive compound.

1-drop or 500 uls of the product is then added to the microchip. The chip is placed into the probe assembly and read immediately before the product dries on the chip.

Figure 10:
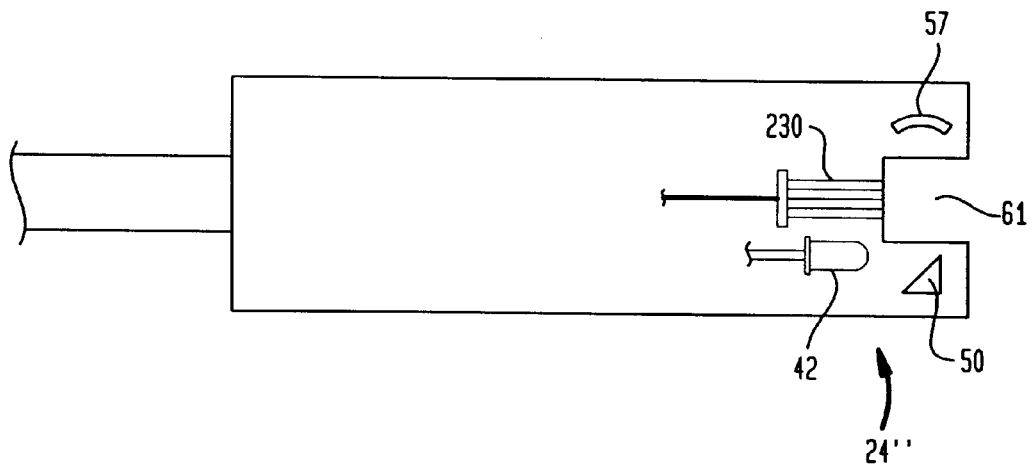

As shown in the embodiment of FIG. 10, a probe assembly 24" may include a plurality of fiber optic cables 230. A chip 200 is inserted into the opening 61. The fiber optic cables are arranged to receive light emitted from a corresponding sample in a corresponding microwell.

EXAMPLE #1

Detection of Authentic Guinness Beer

In this example the product are Guinness, Beamish and Murphy's stout. The products are diluted 1/20 with water. Using the automated system for product identification described in U.S. Pat. No. 5,753,511, a combination of light-emissive compounds are identified. For Guinness, authentication light-emissive compound 33 (stock 10 mM in dimethylsulfoxide DMSO) is mixed with light-emissive compound 17 (stock concentration is 10 mM in DMSO). The working concentration is 30 microliters of light-emissive compound 33 and 10 microliters of light-emissive compound 17 placed in 10 mls of water. Then 340 microliters of the working light-emissive compound concentration is added to 3,000 microliters of the diluted products.

The light-emitting diode wavelength and the filters are easily placed in the probe assembly to match the excitation and emission maximum for the product/light-emissive compound mixture. As discussed above, other products will require matching the light-emitting diode and filters for each product. For this example, the excitation maximum is 490 nanometers and the emission maximum is 530 nanometers.

The device is then calibrated for ambient background light (by pressing switch 28a in the example described with reference to FIG. 1 or other suitable keys as described with reference to FIGS. 5 and 7). The optical detector is reading the amount of stray light detected only.

The authentic sample plus the light-emissive compounds (500 microliters) are placed into the sample holder. The initial reading of the authentic sample is made in the exact location where the test will be made. This reduces any inaccuracies associated with differential temperature, light, or light-emissive compound concentration. In the example described with reference to FIG. 1, this reading is made by pressing switch 28b. Here, the optical detector is reading the amount of fluorescent light from the sample/light-emissive compound mixture.

The suspect sample plus the light-emissive compounds (500 microliters) are placed into a cleaned or different sample holder. The reading is made in exactly the same manner as the authentic sample. In the example described with reference to FIG. 1, this reading is made by pressing switch 28c. Here, the optical detector is reading the amount of fluorescent light from the sample/light-emissive compound mixture.

The fluorescence reading of the suspect sample is then compared to the fluorescence reading of the authentic sample. Authenticity is determined using the following algorithm:

$$\text{Range } C = [F1 + \%F1_{ni} \text{ to } F1 - \%F1_{nx}] +/- \text{Omega}$$

where:

Range C is the filter width for the authentic product at the test location allowing for authentic production variation plus or minus Omega (a statistical measurement at 99% confidence levels);

$+\%F1_{ni}$=the highest fluorescent value determined for standard production of the authentic sample; and, $-\%F1_{nx}$=the lowest fluorescent value determined for standard production of the authentic sample.

If the suspect sample is outside Range C, then the sample is determined to be non-authentic. Pressing switch 28d in the example of FIG. 1 makes this range calculation C and compares the suspect sample to this range.
Portable Authentication Device Readings:

| Sample | Serial # | Reading |
| --- | --- | --- |
| Guinness, Dublin | 21D8 G4 17: 07 | 145 RFU |
| Beamish, Stout Cork | 28 3 8 20 13: 10 | 118 RFU |
| Murphy's Stout, Cork | L8124C 826 23: 31 | 165 RFU |

Range C for Guiness is +/−2.00
RFU = relative fluorescent units.

EXAMPLE #2

Detection of Authentic Coca-Cola

For the large soft drink companies, it is important to verify that the authentic concentrate is being used to make their finished product. In this example the products are Coca-Cola and RC Cola. The products are diluted 1/20 with water. Using the automated system for product identification described in U.S. Pat. No. 5,753,511, a combination of light-emissive compounds are identified. For Coca-Cola authentication light-emissive compound 33 (stock 10 mM in dimethylsulfoxide DMSO). The working concentration is 40 microliters of light-emissive compound 33 placed in 10 mls of water. Then 300 microliters of the working light-emissive compound concentration is added to 3,000 microliters of the diluted products. For this example the excitation maximum is 490 nanometers and the emission maximum is 530 nanometers.

The device is then calibrated, the authentic sample mixture is read, and the suspect sample mixture is read, all as described above in Example 1.
Portable Authentication Device Readings:

| Sample | Serial # | Reading |
| --- | --- | --- |
| Coca-Cola Classic | Jun1499KHB 50710Oct157 | 29 RFU |
| RC Cola | Worcester, MA. | 55 RFU |
| Coca-Cola Namibia | Namibia | 69 RFU |
| RC Cola | Middle East | 76 RFU |
| Coca-Cola, Lahore | Middle East | 56 RFU |

EXAMPLE #3

Authentication of Pharmaceuticals

It may be desirable, for example, for Pharmaceutical Companies to detect compounds infringing a patent. Additionally, low quality copies of patented pharmaceutical companies represent a significant health concern. One scenario is that a higher dose of compound (200-mg dose) is cut or diluted. The diluted capsule is then sold as two or more capsules. The following protocol has been developed according to the present invention to test compounds directly in the trade, at custom checkpoints and at the point of manufacture.

A non-steroidal anti-inflammatory compound is formulated in two concentrations, 100 mg and 200 mg capsules. Capsules are first diluted in water (2.5 grams in 50 milliliters of water) and are then filtered with a portable syringe filter 0.45 uM filter. In this example, butanol is added to the solution to prevent product foaming (19 milliliters of sample to 1 milliliter of butanol).

Using the automated system for product identification described in U.S. Pat. No. 5,753,511, one or a combination of light-emissive compounds are identified. In this example, light-emissive compound 16 is used at a dilution of 28 microliters/10 milliliters of water. Light-emissive compound 16 is equivalent to cat#D2375 (Molecular Probes, Eugene, Oreg.) Light-emissive compound 63 is used at a dilution of 50 microliters/10 milliliters of water. Light-emissive compound 63 is equivalent to cat# F3272 (Sigma Chemical, St. Louis, Mo.)

The 200 mg sample is tested as the authentic sample and the 100 mg sample is tested as the suspect sample.

Portable Authentication Device Readings:

| Sample | Compound 63 | Compound 16 |
|---|---|---|
| 1. 200 mg Sample Lot#1 | 20.47 RFU | 33.28 RFU |
| 2. 200 mg Sample Lot#2 | 20.86 RFU | 32.69 RFU |
| 3. 200 mg Sample Lot#3 | 19.93 RFU | 32.21 RFU |
| 4. 100 mg Sample Lot#4 | 14.27 RFU | 29.00 RFU |
| 5. 100 mg Sample Lot#5 | 17.98 RFU | 30.56 RFU |
| 6. 100 mg Sample Lot#6 | 16.73 RFU | 30.38 RFU |
| Omega Values | 1.78 | 1.66 |

While the best mode for carrying out the invention has been described in detail, those skilled in the art to which this invention relates will recognize various alternative embodiments including those mentioned above as defined by the following claims.

What is claimed is:

1. A portable system for determining the authenticity of a sample, the system comprising:
a portable product authentication device comprising:
a base unit;
a probe assembly coupled to said base unit, with said probe assembly having a light source for irradiating the sample product to be authenticated with a predetermined wavelength of light;
an optical detector for detecting at least one emitted wavelength of light generated by the sample product in response to the irradiating wavelength of light to provide a sample characteristic; and,
a controller disposed within said base unit and communicating with said probe assembly, said controller comparing said sample characteristic to a fingerprint, wherein said fingerprint comprises at least light emission intensity or intensity decay from at least one light-emissive compound in combination with a standard product; and
a chip adapted to receive the sample product and carry the sample product to said portable product authentication device for subsequent authentication, wherein said chip comprises:
a substrate, and
a plurality of different isolated light-emissive compounds attached to a surface of said substrate in a manner whereby the light-emissive compounds will interact with interaction partners, such interaction altering light emission from said light-emissive compounds versus light emission from said light-emissive compounds absent said interaction,
wherein the isolated light-emissive compounds are present in the absence of admixture with other substances,
wherein each of said different light-emissive compounds is attached at a location discrete from attachment of all other of said different light-emissive compounds, and
wherein said substrate is free of interference with light emission from said light-emissive compound in the presence of said interaction and in the absence of said interaction.

2. The system according to claim 1 wherein said light source is a fiber optic cable operatively connected to a light-emitting diode.

3. The system according to claim 1 wherein said light source is a light-emitting diode.

4. The system according to claim 1 wherein said optical detector is disposed within said probe assembly.

5. The system according to claim 1 wherein a fiber optic cable is disposed within said probe assembly and is operatively connected to said optical detector for receiving emitted light generated by the sample product and transmitting to said optical detector.

6. The system according to claim 1 further comprising a receptacle for interchangeably receiving one of a plurality of light sources, with each said light source being selected to emit a desired wavelength of light based on a desired sample product to be authenticated.

7. The system according to claim 1 wherein said probe assembly comprises an emission filter for filtering undesired wavelengths of light from said at least one emitted wavelength of light generated by the sample product in response to the irradiating wavelength of light.

8. The system according to claim 7 wherein said probe assembly is adapted to interchangeably receive one of a plurality of emission filters, with each said emission filter being selected to filter undesired wavelengths of light based on a desired sample product to be authenticated.

9. The system according to claim 1 wherein said probe assembly comprises a source filter for filtering undesired wavelengths of light generated from said light source.

10. The system according to claim 9 further comprising a receptacle for interchangeably receiving one of a plurality of source filters, with each said source filter being selected to filter undesired wavelengths of light based on a selected light source.

11. The system according to claim 1 wherein said optical detector detects a quantity of said at least one emitted wavelength of light generated by the sample product.

12. The system according to claim 1 wherein said optical detector detects a change in quantity over time of said at least one emitted wavelength of light generated by the sample product.

13. The system according to claim 1 wherein said controller is located at a site remote from said probe assembly.

14. The system according to claim 1 wherein said controller comprises a database of stored fingerprints.

15. The system according to claim 1 wherein said optical detector detects a characteristic of a sample known to be authentic to provide said fingerprint.

16. The system according to claim 1 wherein said optical detector performs a plurality of detections on a single sample product to be authenticated.

17. The system according to claim 1 wherein the sample product is one of a liquid sample product and a dry powder sample product.

18. The system according to claim 17 wherein said probe assembly further includes a receptacle adapted to receive said chip.

19. The system according to claim 1 wherein said probe assembly comprises a reflector to reflect light emitted from said light source toward said sample product.

20. The system according to claim 1 wherein said fingerprint includes a range of acceptable fingerprints.

21. The system according to claim 1 wherein said plurality is selected from the group consisting of three different light-emissive compounds, four different light-emissive compounds, five different light-emissive compounds, six different light-emissive compounds, seven different light-emissive compounds, eight different light-emissive compounds and nine different light-emissive compounds.

22. The system according to claim 21 wherein said light-emissive compounds are dyes.

23. The system according to claim 21 wherein said chip defines a plurality of microwells, and wherein said discrete location of attachment of each of said different light-emissive compounds is within a microwell.

24. The system according to claim 23 further comprising one or more markings on said chip for identifying said location of each of said different light-emissive compounds of the chip.

25. The system according to claim 21 further comprising one or more markings on said chip for identifying said location of each of said different light-emissive compounds on said chip.

26. The system according to claim 21 further comprising one or more markings on said chip to identify what different light-emissive compounds are on said chip.

27. The system according to claim 21 wherein said light-emissive compounds are covalently attached to said substrate.

28. The system according to claim 1 wherein said different light-emissive compounds on said chip are preselected and are at a preselected concentration to create a preselected pattern of light emission when said surface is contacted with a sample product that is authentic.

29. The system according to claim 28 further comprising a marking on said chip identifying said chip as specific for the standard product.

30. A portable system for determining the authenticity of a sample product, the system comprising:
  a hand-held probe assembly for detecting a characteristic of the sample product to be authenticated, with said probe assembly comprising:
    a probe body;
    a light source disposed in said probe body for irradiating the sample product with a predetermined wavelength of light; and,
    an optical detector disposed in said probe body for detecting at least one emitted wavelength of light generated by the sample product in response to the irradiating wavelength of light to provide a sample characteristic, wherein said sample characteristic comprises at least light emission intensity or intensity decay from at least one light-emissive compound in combination with the sample product; and
  a chip adapted to receive the sample product and carry the sample product to said probe assembly for subsequent authentication, wherein said chip comprises:
    a substrate, and
    a plurality of isolated different light-emissive compounds attached to a surface of said substrate in a manner whereby the light-emissive compounds will interact with interaction partners, such interaction altering light emission from said light-emissive compounds versus light emission from said light-emissive compounds absent said interaction,
    wherein the isolated light-emissive compounds are present in the absence of admixture with other substances,
    wherein each of said different light-emissive compounds is attached at a location discrete from attachment of all other of said different light-emissive compounds, and
    wherein said substrate is free of interference with light emission from said light-emissive compound in the presence of said interaction and in the absence of said interaction.

31. The system according to claim 30 wherein said light source is a light-emitting diode.

32. The system according to claim 30 further comprising a light-emitting diode receptacle formed in said body for interchangeably receiving one of a plurality of light-emitting diodes, with each said light-emitting diode being selected to emit a desired wavelength of light based on a desired sample product to be authenticated.

33. The system according to claim 30 further comprising an emission filter disposed in said body for filtering undesired wavelengths of light from said at least one emitted wavelength of light generated by the sample product in response to the irradiating wavelength of light.

34. The system according to claim 33 further comprising an emission filter receptacle formed in said body for interchangeably receiving one of a plurality of emission filters, with each said emission filter being selected to filter undesired wavelengths of light based on a desired sample product to be authenticated.

35. The system according to claim 30 further comprising a source filter disposed in said body for filtering undesired wavelengths of light generated from said light source.

36. The system according to claim 35 further comprising a source filter receptacle formed in said body for interchangeably receiving one of a plurality of source filters, with each said source filter being selected to filter undesired wavelengths of light based on a selected light source.

37. The system according to claim 30 wherein said probe body includes a receptacle adapted to receive said chip.

38. The system according to claim 30 further comprising a reflector disposed in said body for reflecting light emitted from said light source toward said sample product.

39. The system according to claim 30 wherein said plurality is selected from the group consisting of three different light-emissive compounds, four different light-emissive compounds, five different light-emissive compounds, six different light-emissive compounds, seven different light-emissive compounds, eight different light-emissive compounds and nine different light-emissive compounds.

40. The system according to claim 39 wherein said light-emissive compounds are dyes.

41. The system according to claim 39 wherein said chip defines a plurality of microwells, and wherein said discrete location of attachment of each of said different light-emissive compounds is within a microwell.

42. The system according to claim 41 further comprising one or more markings on said chip for identifying said location of each of said different light-emissive compounds of the chip.

43. The system according to claim 39 further comprising one or more markings on said chip for identifying said location of each of said different light-emissive compounds on said chip.

44. The system according to claim 39 further comprising one or more markings on said chip to identify what different light-emissive compounds are on said chip.

45. The system according to claim 39 wherein said light-emissive compounds are covalently attached to said substrate.

46. The system according to claim 30 wherein said different light-emissive compounds on said chip are preselected and are at a preselected concentration to create a preselected pattern of light emission when said surface is contacted with a sample product that is authentic.

47. The system according to claim 46 further comprising a marking on said chip identifying said chip as specific for the standard product.

48. A portable system for determining the authenticity of a sample product, the system comprising:
  a portable product authentication device comprising:

a base unit;

a probe assembly for detecting a characteristic of the sample product to be authenticated, said probe assembly contained within said base unit, said probe assembly comprising:

a light source for irradiating the sample product with a predetermined wavelength of light; and, an optical detector for detecting at least one emitted wavelength of light generated by the sample product in response to the irradiating wavelength of light to provide a sample characteristic; and a controller disposed within said base unit and communicating with said probe assembly, said controller comparing said sample characteristic to a fingerprint, wherein said fingerprint comprises at least light emission intensity or intensity decay from at least one light-emissive compound in combination with a standard product; and a chip adapted to receive the sample product and carry the sample product to said portable product authentication device for subsequent authentication, wherein said chip comprises:

a substrate, and a plurality of isolated different light-emissive compounds attached to a surface of said substrate in a manner whereby the light-emissive compounds will interact with interaction partners, such interaction altering light emission from said light-emissive compounds versus light emission from said light-emissive compounds absent said interaction, wherein the isolated light-emissive compounds are present in the absence of admixture with other substances, wherein each of said different light-emissive compounds is attached at a location discrete from attachment of all other of said different light-emissive compounds, and wherein said substrate is free of interference with light emission from said light-emissive compound in the presence of said interaction and in the absence of said interaction.

49. The system according to claim 48 wherein said sample is one of a liquid sample product and a dry powder sample product.

50. The system according to claim 48 wherein said probe assembly further includes a receptacle adapted to receive said chip.

51. The system according to claim 48 wherein said device performs a plurality of sample readings on said chip.

52. The system according to claim 48 wherein said plurality is selected from the group consisting of three different light-emissive compounds, four different light-emissive compounds, five different light-emissive compounds, six different light-emissive compounds, seven different light-emissive compounds, eight different light-emissive compounds and nine different light-emissive compounds.

53. The system according to claim 52 wherein said light-emissive compounds are dyes.

54. The system according to claim 52 wherein said chip defines a plurality of microwells, and wherein said discrete location of attachment of each of said different light-emissive compounds is within a microwell.

55. The system according to claim 54 further comprising one or more markings on said chip for identifying said location of each of said different light-emissive compounds of the chip.

56. The system according to claim 52 further comprising one or more markings on said chip for identifying said location of each of said different light-emissive compounds on said chip.

57. The system according to claim 52 further comprising one or more markings on said chip to identify what different light-emissive compounds are on said chip.

58. The system according to claim 52 wherein said light-emissive compounds are covalently attached to said substrate.

59. The system according to claim 48 wherein said different light-emissive compounds on said chip are preselected and are at a preselected concentration to create a preselected pattern of light emission when said surface is contacted with a sample product that is authentic.

60. The system according to claim 59 further comprising a marking on said chip identifying said chip as specific for the standard product.

* * * * *

UNITED STATES PATENT AND TRADEMARK OFFICE
CERTIFICATE OF CORRECTION

PATENT NO.      : 6,490,030 B1
DATED           : December 3, 2002
INVENTOR(S)     : Richard Selinfreund et al.

It is certified that error appears in the above-identified patent and that said Letters Patent is hereby corrected as shown below:

<u>Title page,</u>
Item [75], Inventors, "Richard P. Gill, Ledyard, CT (US); Rakesh Vig, Durham, CT (US); J. Christopher Philips, Charlestown, RI (US); Friedrich Behringer, Old Lyme, CT (US)" should read
-- Richard Selinfreund, Branford, CT
Richard P. Gill, Ledyard, CT; Rakesh Vig, Durham, NC
J. Christopher Philips, Charlestown, RI; Friedrich Behringer, Oldlyme, CT --

Signed and Sealed this

Thirty-first Day of December, 2002

JAMES E. ROGAN
*Director of the United States Patent and Trademark Office*